(12) United States Patent
DiSilvestro et al.

(10) Patent No.: US 7,218,232 B2
(45) Date of Patent: May 15, 2007

(54) ORTHOPAEDIC COMPONENTS WITH DATA STORAGE ELEMENT

(75) Inventors: Mark DiSilvestro, Fort Wayne, IN (US); Robert Hastings, Warsaw, IN (US); Terry Dietz, Columbia City, IN (US)

(73) Assignee: Depuy Products, Inc., Warsaw, IN (US)

( * ) Notice: Subject to any disclaimer, the term of this patent is extended or adjusted under 35 U.S.C. 154(b) by 108 days.

(21) Appl. No.: 10/813,292

(22) Filed: Mar. 30, 2004

(65) Prior Publication Data

US 2005/0012617 A1 Jan. 20, 2005

Related U.S. Application Data

(60) Provisional application No. 60/486,614, filed on Jul. 11, 2003.

(51) Int. Cl.
*G08B 13/14* (2006.01)
(52) U.S. Cl. .............................. 340/572.8; 340/572.1; 340/573.1; 600/300; 235/375
(58) Field of Classification Search ............ 340/572.1, 340/572.8, 573.1, 539.12; 128/98; 600/300; 235/375, 492
See application file for complete search history.

(56) References Cited

U.S. PATENT DOCUMENTS

| 5,300,120 | A | | 4/1994 | Knapp et al. |
| 5,383,915 | A | * | 1/1995 | Adams ..................... 607/60 |
| 6,239,705 | B1 | * | 5/2001 | Glen ..................... 340/573.1 |
| 6,400,272 | B1 | * | 6/2002 | Holtzman et al. ....... 340/572.1 |
| 6,447,448 | B1 | | 9/2002 | Ishikawa et al. |
| 6,687,131 | B1 | | 2/2004 | Miehling |
| 6,947,004 | B2 | * | 9/2005 | Mejia et al. ............... 343/787 |
| 2004/0008123 | A1 | * | 1/2004 | Carrender et al. ..... 340/825.49 |

OTHER PUBLICATIONS

Want, Roy, "RFID-A Key to Automating Everything", Jan. 2004, (13 pages).

* cited by examiner

*Primary Examiner*—Anh V. La

(57) ABSTRACT

An implantable orthopaedic component includes an information storage device that contains information related to the component. In the preferred embodiment, the information storage device is an RFID tag that is embedded within the component or within a housing that is configured to be removably engaged to the component. The RFID tag can be pre-loaded with information related only to the implant, or can be configured to allow additional surgery or patient specific information to be added by the caregiver at the time and point of surgery.

16 Claims, 2 Drawing Sheets

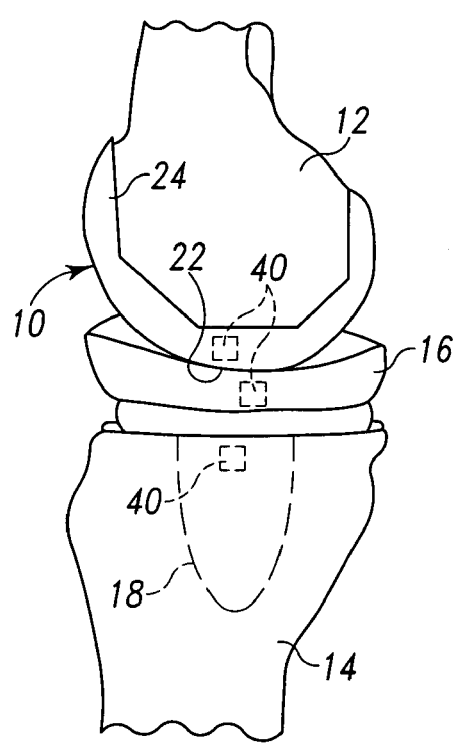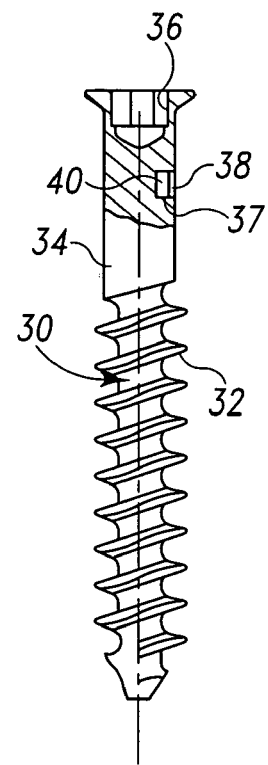
Fig. 1　　　Fig. 2
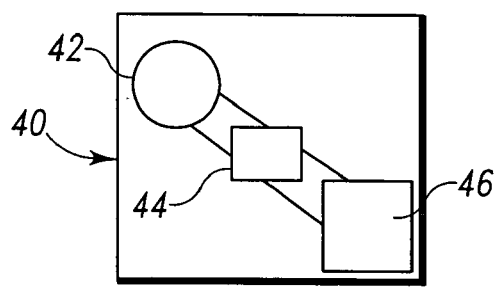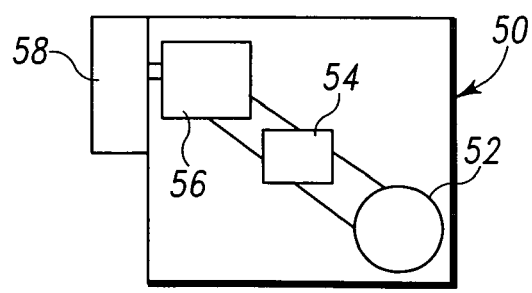
Fig. 3　　　Fig. 4

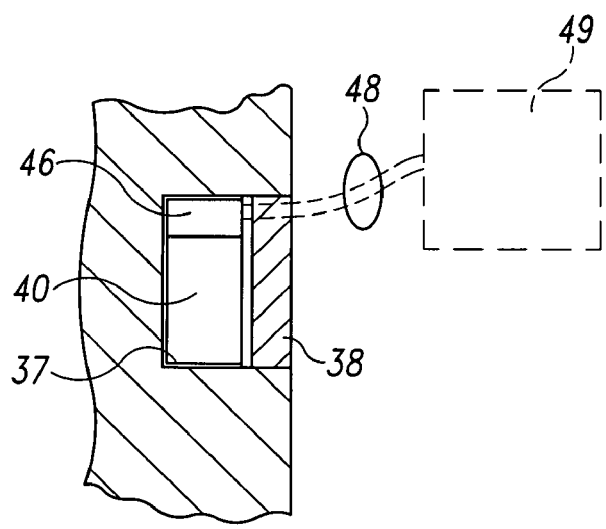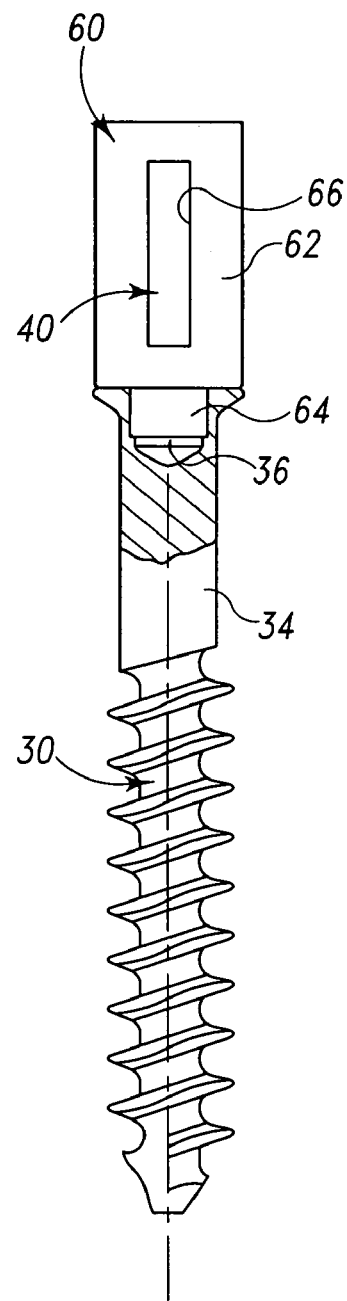
Fig. 5
Fig. 6

ORTHOPAEDIC COMPONENTS WITH DATA STORAGE ELEMENT

CROSS-REFERENCE TO RELATED APPLICATION

This application claims priority to U.S. Provisional No. 60/486,614, entitled "ORTHOPAEDIC ELEMENT WITH SELF-CONTAINED DATA STORAGE", which was filed on Jul. 11, 2003, in the name of common inventors. The disclosure of this provisional application 60/486,614 is incorporated herein by reference.

FIELD OF THE INVENTION

The present invention relates to orthopaedic components configured for implantation within a patient. In particular, the invention concerns a component associated with the orthopaedic component that carries stored data related to the implant.

BACKGROUND OF THE INVENTION

Joint endoprostheses have been developed to replace virtually every human joint. As life expectancy increases, people are increasingly likely to require replacement of a joint that simply wears out from years of use. For instance, knee and hip prostheses are becoming more commonplace among the aging population. The success of these orthopaedic components or implants has steadily increased over the years as improvements in materials, manufacturing and design are developed.

It is desirable for manufacturers of orthopaedic components and orthopaedic surgeons to track the products once they leave the manufacturing floor and post-operatively. This tracking can be part of the inventory control for both the manufacture and the end user hospital. It can also form part of the manufacturer quality control and can even expedite patient care by providing valuable information about the associated orthopaedic component. For a variety of reasons, some joint endoprostheses require replacement or revision many years after implantation. Identification of the implant can provide valuable information regarding the implant design and its manufacture.

Until now, tracking the history of an orthopaedic implant has been left to written records or retention in a computer database. Where the records are only used for inventory control, this manner of recording the implant information is usually sufficient. However, many records of this sort are kept handy for a limited time, so that the recorded information may not be available for a revision procedure many years later. Consequently, there is a need for a system to maintain information concerning an orthopaedic implant that is associated with the implant and readily accessible at any point in the life of the implant.

SUMMARY OF THE INVENTION

To address these needs, the present invention contemplates an orthopaedic component for engagement to the human body that comprises a component body and an RFID tag configured for storing information related to the orthopaedic component, said RFID tag associated with said component body so that the stored information can be accessed by an independent reader.

In certain embodiments, the RFID tag is embedded within the component body. Where the component body is a molded body, the RFID tag is molded within the molded body. In machined orthopaedic components, the component body defines a cavity sized to receive the RFID tag therein. The component body may include a cover closing the cavity with the RFID tag embedded therein. Preferably, the cover is a biocompatible potting material, such as a bone cement. Alternatively, the cover material may be a biocompatible metal, polymer, or composite.

The RFID tag includes a transmission receiver configured for receiving external transmissions, an information storage element, and a control circuit electrically connected between the receiver and the storage element. The control circuit is operable to activate the storage element in response to an external transmission. The transmission receiver operates as a passive power supply for the RFID tag. The information storage element preferably includes an EEPROM into which data can be readily stored using a conventional writing device.

In other embodiments, the RFID tag is embedded within a cavity defined in a housing independent of the orthopaedic component. The housing and the orthopaedic component define an engagement feature therebetween that allows the housing to be discarded after the RFID tag information has been read. In a preferred embodiment, the engagement feature includes a recess defined in the component body, and an engagement element defined on the housing. The engagement element is configured for engagement within the recess, and particularly by a press-fit, taper-fit, snap-fit or the like.

The invention further contemplates a method for associating information related to an orthopaedic component with that component comprising the steps of storing information related to the orthopaedic component in an information storage device, engaging the information storage device to the orthopaedic component, and remotely accessing the information stored in the information storage device. The remote access can be accomplished with a remote reader that is compatible with the information storage device. In a preferred embodiment, the reader and storage device are RFID components that are capable of transmitting RF signals through the human body as well as in or around metallic components.

In certain applications, the step of remotely accessing occurs before the orthopaedic component is implanted in a patient. In these applications, the accessed information can be used to identify the particular implant and verify that it is the proper implant for the upcoming procedure. The stored information can be stored in the information storage device during the manufacture of the orthopaedic component and can include one or more of the following: product identification; part number; batch number; manufacturer; manufacture date; and inspection information.

In other applications, the step of remotely accessing occurs after the orthopaedic component is implanted in a patient. For instance, the information can be accessed by airport security personnel to verify that the triggering metal element is an orthopaedic component. The information can also be accessed in a subsequent surgery, or in a later revision surgery.

In still other applications, the inventive method contemplates that the stored information is stored in the information storage device by the caregiver implanting the orthopaedic component. This stored information can include one or more of the following: patient identification; patient medical history; caregiver information; and date of implant surgery.

This information can be used to track the implant during its life and even provide information useful for a revision procedure.

It is one object to provide a system for associating important information with an orthopaedic implant, in which the information can be used, at a minimum, to identify the particular implant component. It is a further object to provide such a system that permits the storage and retrieval of other information related to the implant, to the patient and even to the surgical procedure in which the orthopaedic component was implanted within the patient.

Other object and certain benefits of the invention will become apparent from the following written description, taken together with the accompanying figures.

DESCRIPTION OF THE FIGURES

FIG. 1 is a side elevation of a knee joint endoprosthesis implanted between the distal femur and proximal tibia, with the endoprosthesis modified in accordance with one embodiment of the present invention.

FIG. 2 is a side partial cross-sectional view of a bone fastener modified in accordance with one embodiment of the present invention.

FIG. 3 is a schematic representation of an RFID tag embedded within the endoprosthesis of FIG. 1 and the bone fastener of FIG. 2.

FIG. 4 is a schematic representation of a reader for reading the information stored in the RFID tag of FIG. 3.

FIG. 5 is an enlarged cross-sectional view of the RFID tag shown in FIG. 2 with an external writing device connected to the information storage element of the tag.

FIG. 6 is a side elevation of a bone fastener with an RFID tag engaged thereon according to a further embodiment of the invention.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a remotely accessible data storage element associated with an orthopaedic component or implant. While only certain implants are discussed herein, it is understood that the principles of this invention can be applied to a wide range of implants, including, but not limited to, joint endoprostheses, bone fasteners such as bone screws, fixator systems, bone plates and the like.

A representative knee joint endoprosthesis 10 is illustrated in FIG. 1. The knee joint endoprosthesis 10 is implanted between the distal end of the femur 12 and the proximal end of the tibia 14. The endoprosthesis includes a tibial bearing 16 carried by a proximal tibial component 18 that is affixed to the tibia 14. The tibial bearing has a contoured proximal surface against which the condyles 22 of a distal femoral component 24 bear. The distal femoral component 24 is affixed to the femur 12.

The elements of the knee endoprosthesis are typically formed of standard medical grade metals, such as cobalt-chrome or titanium. Some elements, such as the tibial bearing, are usually made of non-metallic materials, such as polyethylene or ceramic.

A bone fastener 30 is illustrated in FIG. 2. The fastener includes a bone engaging portion 32, which can be in the form of bone threads as depicted in the figure. The fastener 30 includes a head portion 34 that terminates in a driving feature 36 which can be a recess configured to receive a standard driving tool used to thread the fastener into a bone. The fastener 30 is typically formed of a medical grade metal, such as titanium or cobalt-chrome.

Each of the implant components described above—i.e., the proximal tibial component 18, the distal femoral component 24, the tibial bearing 16 and the bone fastener 30—are all provided with a remotely accessible information storage device 40. In one embodiment of the invention, the storage device 40 is embedded within the particular component. The element can be embedded within the component when it is produced, such as by supporting the device 40 within a mold while forming the orthopaedic component around the element. This approach is best suited for non-metallic components, such as the tibial bearing 16 that can be molded from a polymer, such as polyethylene.

For the metallic components, forming the component around the storage element 40 can be more problematic. In an alternative embodiment, a cavity can be formed in the component, such as the cavity 37 defined in the head portion 34 of the fastener 30 shown in FIG. 2. The cavity is formed in an area of the implant that does not compromise the mechanical properties of the component. The information storage device 40 can be embedded within the cavity 37 and then concealed behind a cover 38. The cover can be formed of a biocompatible metal, but is preferably a bio-compatible potting material that seals the cavity against bodily fluids and tissue ingrowth. For instance, the potting material can be an orthopaedic bone cement such as poly-methylmethacrylate, a biocompatible epoxy or a liquid sealant such as polyurethane or silicone. For certain implants, the cover 38 can be a threaded cap for engaging internal threads of the cavity.

In accordance with one embodiment of the invention, the information storage device is an RFID tag. As shown schematically in FIG. 3, the RFID tag 40 includes a transmission receiver 42. The receiver is typically in the form of a magnetic coil for low frequency RFID systems, or in the form of a dipole antenna for high frequency applications. A suitable coil is a small wound ferrite coil available from Microhelix Inc. of Portland, Oreg. The transmission receiver 42 is electrically connected to a control circuit 44 that is responsive to an electric current produced by the receiver when it receives an external transmission. The control circuit 44 is connected to a storage element 46 that includes implant specific information, as discussed below.

In a preferred embodiment, the device 40 can be of the type described in U.S. Pat. No. 6,687,131 (the '131 patent), assigned to Sokymat S. A of Switzerland. The disclosure of the '131 patent is incorporated herein by reference. The '131 patent discloses a transponder that includes an integrated circuit, an antenna and a coil that is encapsulated within a thermoplastic resin and that is particularly suited for placement within an injection molded part or within a cavity or pocket in a machined part.

The information stored within the RFID tag 40 is accessed by a reader 50, illustrated schematically in FIG. 4. The reader 50 includes a transmitter element 52 that can constitute a power coil for low frequency devices or a dipole transmitter for high frequency systems. The transmitter element 52 is coupled to a conversion circuit 54. In a low frequency device, the conversion circuit includes an oscillator that energizes the power coil and an analog-to-digital converter that converts variations in the power coil current to digital signals. For a high frequency device, the conversion circuit constitutes a transceiver that energizes the dipole antenna and measures variations in a reflected signal received by the antenna. The transmitter element 52 receives and sends signals to an integrated circuit 56 that controls the operation of the antenna and prepares the incoming signal for viewing on a display 58.

In both low frequency and high frequency devices, the RFID tag 40 is actively powered or passively powered by transmissions from the reader 50 to the transmission receiver 42. In the latter case, the tag 40 does not require an internal power supply that can be exhausted over time or that can pose a leakage problem when implanted. The storage element 46 can be an integrated circuit that is configured to generate a digital signal corresponding to the information intended to be stored. This digital signal is fed back through the control circuit 44 which varies the resistance in the magnetic circuit including the low frequency power coil or varies the amplitude of a reflected RF signal in high frequency applications, to transmit the encoded information stored in the tag 40. The integrated circuit 56 in the reader is correspondingly configured to translate the digital signal to a human readable format.

In accordance with the present invention, the information storage device 40 can carry specific information about the implant itself. For instance, the stored information can include any of the facts: manufacturer, material, part number, product version or release number, catalog number, lot or batch number, manufacturing or inspection release date, or shipping date. The nature of the stored information will depend on when the storage element is embedded within the orthopaedic component and on the nature of the storage element 46 of the RFID tag 40. In a specific embodiment, the storage element is an EEPROM that is electrically connected to a writing device to electronically write the necessary information to the EEPROM. Nominally, the EEPROM will be written to before the storage device 40 is embedded within the implant. In that case, the recorded information cannot include data about events that have yet to occur in the life of the implant, such as inspection and shipment dates.

Alternatively, communication means 48 can be provided to connect an embedded storage device 40 to the electronic writing device. For instance, electrical leads connected to the storage element or EEPROM 46 can extend outside the implant within which the storage device 40 is embedded. As represented in FIG. 5, leads 48 can be connected to an external writing device 49 of known configuration to enter the appropriate implant information. Once the new information has been written to the EEPROM 46, the leads 48 can be severed or potted over with a sealant compound, such as bone cement.

It is also envisioned that remote writing features can be provided to the storage element 46 that allow writing to an embedded device by RF transmission. In this case, the control circuit 44 would be modified to permit switching the storage device 40 between "read" and "write" configurations. This data can be written via the transmission receiver 42 of FIG. 3 or through the communication means 48 of FIG. 5. When the storage device contemplates remote writing of an EEPROM, it may be desirable to include multiple EEPROMs within the storage element 46. One EEPROM can be dedicated to identifying the type of implant, its material, the product version and its manufacturer, or other information that is not dependent upon the events subsequent to when the storage device itself is produced. The second EEPROM can store information that is event dependent, such as manufacture date or shipping date. Alternatively, the information stored on the device 40 can provide access to an external data base that associates other implant and/or patient specific information to the particular device.

Providing "read/write" capability to the storage device 40 expands the type of relevant information that can be associated with a given orthopaedic implant. The information discussed above has been specific to the implant itself. Information that is specific to the caregiver or patient can also be written to the storage device 40. For example, such information can include hospital, surgeon, and date of the surgery. If the storage element 46 has sufficient memory capability, other information can include notes of the surgery or the patient's medical history related to the need for the orthopaedic implant, or even x-ray images of the implant in vivo. This information can be recorded by the caregiver before, during or after the surgery so that the pertinent information will be available at a later time and to a different caregiver.

It can even be envisioned that information can be written to the device 40 when its associated orthopaedic component is implanted within the patient. For instance, the stored medical information can be updated in follow-up check-ups, noting any problems. In this case, the storage device 40 and reader 50 must be capable of transmitting and receiving through body tissue.

The information available on the device 40 can be valuable if the patient is undergoing treatment many years after the implant surgery, or for emergency room treatment where medical records may not be readily available. In addition, the device 40 can be read by security personnel when an implant triggers a security sensor.

From the standpoint of the implant manufacturer, the information stored in the device 40 can provide valuable post-surgery information about its orthopaedic implants. For example, the date that an orthopaedic component was implanted can be compared to the date of its removal in a revision surgery. This information, coupled with a visual assessment of the implant, can provide data about the life of the implants. The condition of the implant can be correlated to the implant specific information stored in the device 40, such as material or manufacturing batch.

In an alternative embodiment, the information storage device 40 is integrated into a removable tag. As shown in FIG. 6 a tag 60 is configured to be removably mounted to the bone fastener 30 described above. The tag 60 includes a housing 62 with an engagement element 64 that is configured to be press-fit within the driving feature 36. The housing 62 defines a cavity 66 for receiving the information storage device 40. The housing 62 can be formed of an injection moldable plastic that is preferably sterilizable. Preferably, the information storage device 40 is embedded within the housing as the housing is molded.

In this embodiment, the removable tag 60 stores sufficient information to identify the associated orthopaedic implant, such as the fastener 30. The caregiver can use the reader 50 to query the embedded information storage device 40 to identify the part. This information can be used to verify that the implant is correct or can be used for inventory control. Once the information has been read, the tag 60 can de discarded or retained as a record of the orthopaedic components implanted by a caregiver.

The tag 60, and particularly the engagement element 64 is illustrated in FIG. 6 engaged within the driving feature or recess 36 of a bone fastener. However, it is understood that the engagement element 64 can be modified to accommodate similar features in other implants. Many orthopaedic components include recesses for engagement by an insertion tool. The engagement element 64 can be modified accordingly for a press-fit within those recesses. One object of the tag 60 is that it remains associated with the implant until the component is needed during the surgical procedure. The caregiver facility can be provided with a reader 50 for use in the pre-operative environment as the tools, instruments and implants are being prepared for surgery. Once the tag has been read to verify the implant, the tag can be discarded.

In a specific embodiment, the information storage device is a glass RFID transponder produced by SOKYMAT Identification USA, Inc. of Cynthiana, Ky. This transponder is a mere 2.12 mm in diameter and 12 mm in length, so that it can be easily housed within a tag 60 or embedded within many orthopaedic implants. This particular transponder can withstand ETO, gas plasma, and autoclave sterilization. It is important that the transponder or RFID tag be capable of operating in or around metal objects. Depending upon the nature of the implant, it may also be important for the tag to be able to withstand gamma radiation sterilization.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An orthopaedic component for engagement to a human body, comprising:
   a component body defining a cavity sized to receive a radio frequency identification (RFID) tag therein;
   the RFID tag configured for storing information related to the orthopaedic component, said RFID tag associated with said component body so that the stored information can be accessed by an independent reader; and
   a cover for closing said cavity with said RFID tag within said cavity.

2. The orthopaedic component of claim 1, wherein:
   said component body is a molded body; and
   said RFID tag is molded within said molded body.

3. The orthopaedic component of claim 1, wherein said cover is a biocompatible potting material.

4. The orthopaedic component of claim 3, wherein said potting material is a bone cement.

5. The orthopaedic component of claim 1, wherein said cover is a biocompatible metal, a biocompatible polymer, or a biocompatible composite material.

6. The orthopaedic component of claim 1, wherein said RFID tag includes:
   a transmission receiver configured for receiving external transmissions;
   an information storage element; and
   a control circuit electrically connected between said receiver and said storage element and operable to activate said storage element in response to an external transmission.

7. The orthopaedic component of claim 6, wherein said transmission receiver operates as a passive power supply for said RFID tag.

8. The orthopaedic component of claim 6, wherein said information storage element has read/write capabilities.

9. The orthopaedic component of claim 8, wherein said information storage element includes an EEPROM; and
   said orthopaedic component replaces at least a portion of a bone in a joint.

10. An orthopaedic component for engagement to a human body, comprising:
    a component body;
    a radio frequency identification (RFID) tag configured for storing information related to the orthopaedic component, said RFID tag associated with said component body so that the stored information can be accessed by an independent reader;
    a housing defining a cavity sized for receiving said RFID tag therein;
    an engagement feature defined between said housing and said component body, said engagement feature including a recess defined in said component body and an engagement element defined on said housing, wherein said engagement element is configured for press-fit engagement within said recess.

11. The orthopaedic component of claim 10, wherein said engagement element is configured for a taper-fit engagement.

12. The orthopaedic component of claim 10, wherein the RFID tag stores information including one or more of the following:
    product identification;
    part number;
    batch number;
    manufacturer;
    manufacture date; and
    inspection information.

13. The orthopaedic component of claim 10, wherein the RFID tag stores information including one or more of the following:
    patient identification;
    patient medical history;
    caregiver information; and
    date of implant surgery.

14. An orthopaedic component for engagement to a human body, comprising:
    a component body;
    a radio frequency identification (RFID) tag configured for storing information related to the orthopaedic component, said RFID tag associated with said component body so that the stored information can be accessed by an independent reader;
    a housing defining a cavity sized for receiving said RFID tag therein;
    an engagement feature defined between said housing and said component body, said engagement feature including a recess defined in said component body and an engagement element defined on said housing, wherein said engagement element is configured for slip-fit, snap-fit, or threaded fit engagement within said recess.

15. The orthopaedic component of claim 14, wherein the RFID tag stores information including one or more of the following:
    product identification;
    part number;
    batch number;
    manufacturer;
    manufacture date; and
    inspection information.

16. The orthopaedic component of claim 14, wherein the RFID tag stores information including one or more of the following:
    patient identification;
    patient medical history;
    caregiver information; and
    date of implant surgery.

* * * * *